(12) United States Patent
Ahn et al.

(10) Patent No.: US 8,388,937 B2
(45) Date of Patent: Mar. 5, 2013

(54) SPECIFIC PEPTIDE BINDING TO GLYPICAN-3

(75) Inventors: Byeong Cheol Ahn, Daegu (KR); Jae Tae Lee, Daegu (KR); Je Yeol Cho, Daegu (KR); Jung Soo Yu, Daegu (KR); Yong Jin Lee, Anyang-si (KR); Sang Woo Lee, Daegu (KR); You La Lee, Busan (KR)

(73) Assignee: Kyungpook National University Industry—Academic Cooperation Foundation, Daegu (KR)

( * ) Notice: Subject to any disclaimer, the term of this patent is extended or adjusted under 35 U.S.C. 154(b) by 214 days.

(21) Appl. No.: 12/704,877

(22) Filed: Feb. 12, 2010

(65) Prior Publication Data
US 2010/0203612 A1    Aug. 12, 2010

(30) Foreign Application Priority Data

Feb. 12, 2009 (KR) ........................ 10-2009-0011398

(51) Int. Cl.
*A61B 5/055* (2006.01)
(52) U.S. Cl. ...................................... 424/9.34
(58) Field of Classification Search ........................ None
See application file for complete search history.

(56) References Cited

FOREIGN PATENT DOCUMENTS
WO        WO0012711      *  9/2000

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
A_Geneseq_201122 Acc. No. AAY70467 (Jun. 15, 2007) from Au-Young et al, WO2000012711 Sep. 3, 2000. Alignment with SEQ ID No. 1.*
Pilia et al, Mutations in GPC3, a glypican gene, cause the Simpson-Golabi-Behmel overgrowth syndrome. Nat Genet. Mar. 1996;12(3):241-7.*
GenBank AAA98132 from Pilia et al, Nat Genet. Mar. 1996;12(3):241-7.*
Nakatsura et al, Glypican-3, overexpressed specifically in human hepatocellular carcinoma, is a novel tumor marker. Biochem Biophys Res Commun. Jun. 20, 2003;306(1):16-25.*
Nakatsura et al, Identification of glypican-3 as a novel tumor marker for melanoma. Clin Cancer Res. Oct. 1, 2004;10(19):6612-21.*
Baumhoer et al, Glypican 3 expression in human nonneoplastic, preneoplastic, and neoplastic tissues: a tissue microarray analysis of 4,387 tissue samples. Am J Clin Pathol. Jun. 2008;129(6):899-906.*
Aviel-Ronen et al, Glypican-3 is overexpressed in lung squamous cell carcinoma, but not in adenocarcinoma. Mod Pathol. Jul. 2008;21(7):817-25. Epub May 9, 2008.*

* cited by examiner

*Primary Examiner* — Sheridan Swope
(74) *Attorney, Agent, or Firm* — Workman Nydegger

(57) ABSTRACT

A specific targeting peptide binding to glypican-3 can specifically binds to glypican-3 overexpressed in carcinoma cells and includes an amino acid sequence represented by SEQ ID NO:1 or some thereof. Glypican-3 is overexpressed in malignant tumors including hepatocellular carcinoma, melanoma, germ cell tumor, etc., and may be targeted in diagnosis and treatment of tumors by labeling the targeting peptide. A diagnosis using the specific peptide may detect even small tumors more accurately than conventional methods. A treatment method using the specific peptide may remove only carcinoma cells without harming other normal tissues.

10 Claims, 8 Drawing Sheets
(7 of 8 Drawing Sheet(s) Filed in Color)

FIG 1. – SEQ ID NO:1

SEQUENCE LISTING

```
<160> NUMBER OF SEQ ID NOS: 10

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Leu Asn Val Gly Gly Thr Tyr Phe Leu Thr Thr Arg Gln
1               5                   10
```

```
<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Glu Leu His Asn Thr Pro Tyr Gly Thr Ala Ser Glu Pro Ser Glu
1               5                   10                  15

Lys Ala Lys Ile
            20

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Glu Leu His Asn Thr Pro Tyr Gly Thr Ala Ser Glu Pro Ser Glu
1               5                   10                  15

Lys Ala

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Cys Ser Ala Gly Leu Gly Ala Leu Ala Gln Arg Pro Gly Ser Val
1               5                   10                  15

Asp Ser Lys Trp
            20

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Gly Ile Gly Ala Gly Leu Gly Gly Leu Cys Arg Arg
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Gln Phe Ile Glu Asn Gly Ser Glu Phe Ala Gln Lys Leu
1               5                   10

<210> SEQ ID NO 7
<211> LENGTH: 13
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Ser Ile Leu Leu Thr Glu Gln Ala Leu Ala Lys Ala
1               5                   10

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aattagaatt ccaggatggc cgggaccgtc                                      30

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttactctaga gtagcacatg tgctgggca                                       29

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Phe Leu Thr Thr Arg Gln
1               5
```

SPECIFIC PEPTIDE BINDING TO GLYPICAN-3

BACKGROUND

1. Field

Example embodiments relate to a specific peptide binding to glypican-3 protein, and, more particularly, to a peptide which specifically binds to glypican-3 protein overexpressed in some malignant tumors and which may be used in diagnosis and treatment of a corresponding malignant disease while minimizing effects on other normal organs.

2. Description of the Related Art

Hepatocellular carcinoma (HCC) is usually asymptomatic at early stages and has a great propensity for intravascular or intrabiliary invasion, even when the primary tumor is small. As a result, HCC is generally at an advanced stage when discovered and only 10-20% of primary HCCs are found to be resectable at the time of diagnoses.

A molecular marker for screening and diagnosis of HCC is alphafetoprotein (AFP). Although alphafetoprotein occurs only during prenatal life in normal tissues, it is known to be an oncofetal protein due to its reactivated occurrence in many liver cancer cells. AFP concentration decreases gradually after birth to <10 ng/ml in 12-18 months. If AFP levels are 20 ng/ml or higher, 60 to 80% of HCC cases are detected, but sensitivity is significantly lower in the case of small tumors.

The size of a tumor is a significant risk factor for intrahepatic spread and metastasis of HCC. Many more treatment options are available for patients with small tumors while symptomatic tumors are generally large, and often beyond therapeutic intervention. Because the currently used serological test is a sequential AFP analysis which is low in sensitivity, it is difficult to detect tumors when they are small. Another problem with the use of AFP as a marker for HCC is its lack of specificity. Significant increases of AFP are seen in a considerable number of patients with chronic liver diseases. It has been reported that 15-58% of patients with chronic hepatitis, and 11-47% of patients with cirrhosis had increased serum AFP. It is, therefore, not uncommon that serum AFP levels in patients with HCC and cirrhosis overlap, which confounds the interpretation of the results of the AFP assay. In view of the unreliability of AFP levels, most screening regimens include ultrasonography, which is highly sensitive to liver tumors. However, ultrasonography lacks specificity, and cannot reliably distinguish between HCC, cirrhotic nodule, and dysplastic nodule when the lesions are smaller than about 2 cm.

Although there are a number of treatment methods, HCC has been known to be a difficult-to-treat carcinoma due to bad prognostic results compared to other carcinomas. When found in early stages, the carcinoma may be subjected to a surgical therapy for treatment. However, the carcinoma is rarely found in early stages and includes multiple extraheptic metastases, indicating that most surgeries may not be performed for treatment. Although the location and size of HCC is suitable for surgery, in most cases surgical options are not possible due to accompanying liver diseases. For these reasons, in HCC cases which prohibit surgical means, treatments such as transcatheter arterial embolization (TAE), transcatheter arterial chemoembolization (TACE), percutaneous ethanol injection (PEI), percutaneous radiofrequency therapy, and percutaneous radionuclide injection have been tried with limited effects. When treatment has been tried by systemically administering antitumor agents to a patient, partial effects may be obtained and symptoms may be aggravated by secondary side effects of chemotherapies. Thus, if a specific treatment method including binding to antigens specifically overexpressed in HCC were to be developed, it might be a treatment method which would effectively remove only carcinomas without harming other normal tissues. Furthermore, it may be a plausible treatment method for patients whose liver functions are so degraded that no other treatments may be used as well as for all the terminal stage patients.

SUMMARY

Embodiments are directed to a peptide that binds specifically to glypican-3, which substantially overcomes one or more of the problems due to the limitations and disadvantages of the related art.

It is therefore a feature of an embodiment to provide a peptide that binds specifically to glypican-3 protein, which specifically binds to carcinoma cells in which glypican-3 (GPC-3) is expressed, and may be used for diagnosis of the size or location of the tumor and treatment of the carcinoma.

At least one of the above and other features and advantages may be realized by providing a peptide that binds specifically to glypican-3 protein, including an amino acid sequence represented by SEQ ID NO:1.

The peptide that binds specifically to glypican-3 protein may include some of the amino acid sequence represented by SEQ ID NO:1.

At least one of the above and other features and advantages may be realized by providing a kit for diagnosis of carcinomas, including the peptide that binds specifically to glypican-3 protein.

At least one of the above and other features and advantages may be realized by providing a contrast agent for in vivo imaging, including the peptide that binds specifically to glypican-3 protein.

In the kit for diagnosis of carcinoma or contrast agent for in vivo imaging, the peptide may be labeled by a material selected from the group consisting of chromogenic enzyme, radioactive isotope, chromophore, luminescent material, and fluorescent material, or mixtures thereof.

At least one of the above and other features and advantages may be realized by providing a composition for treatment and prophylaxis of carcinomas, including the peptide that binds specifically to glypican-3 protein.

BRIEF DESCRIPTION OF THE DRAWINGS

The patent or application file contains at least one drawing executed in color. Copies of this patent or patent application publication with color drawing(s) will be provided by the office upon request and payment of the necessary fee. The above and other features and advantages will become more apparent to those of ordinary skill in the art by describing in detail, exemplary embodiments with reference to the attached drawings, in which:

FIG. 3 A illustrates a test result of whether GPC-3 gene was expressed using RT-PCR, while FIG. 3 B illustrates a result from observation of whether GPC-3 gene was expressed by Western blot. According to FIGS. 3 A and B, it can be confirmed that GPC-3 protein was expressed in the hepatocellular carcinoma cell lines and the melanoma cell line while GPC-3 protein was not expressed in the renal cell lines. According to FIG. 3 C, it can be confirmed that GPC-3 gene and GPC-3 protein were expressed in the human renal cell line HEK 293 cell by transfection of GPC-3 gene.

DETAILED DESCRIPTION

Korean Patent Application No. 10-2009-0011398 filed on 12 Feb. 2009, in the Korean Intellectual Property Office, and entitled: "Specific peptide binding to glypican-3" is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

Hereinafter, embodiments will be described in detail with reference to the accompanying drawings.

The present invention provides a peptide that binds specifically to glypican-3 (GPC-3) protein. The word "specific" in the present invention refers to the capability not to bind to other proteins, but to target and binds only to glypican-3 protein overexpressed in some malignant tumor cells. The peptide of the present invention may specifically bind to glypican-3 protein expressed in tumor cells for selective screening of glypican-3 protein expression cells and may be used in diagnosis and treatment of the size and location of tumors by using the same. In addition, the peptide of the present invention may specifically bind to glypican-3 overexpressed in hepatocellular carcinoma, melanoma, germ cell tumor, some pulmonary carcinoma and liposarcoma, etc., and may allow accurate diagnosis and treatment of the carcinomas.

Figure 1:
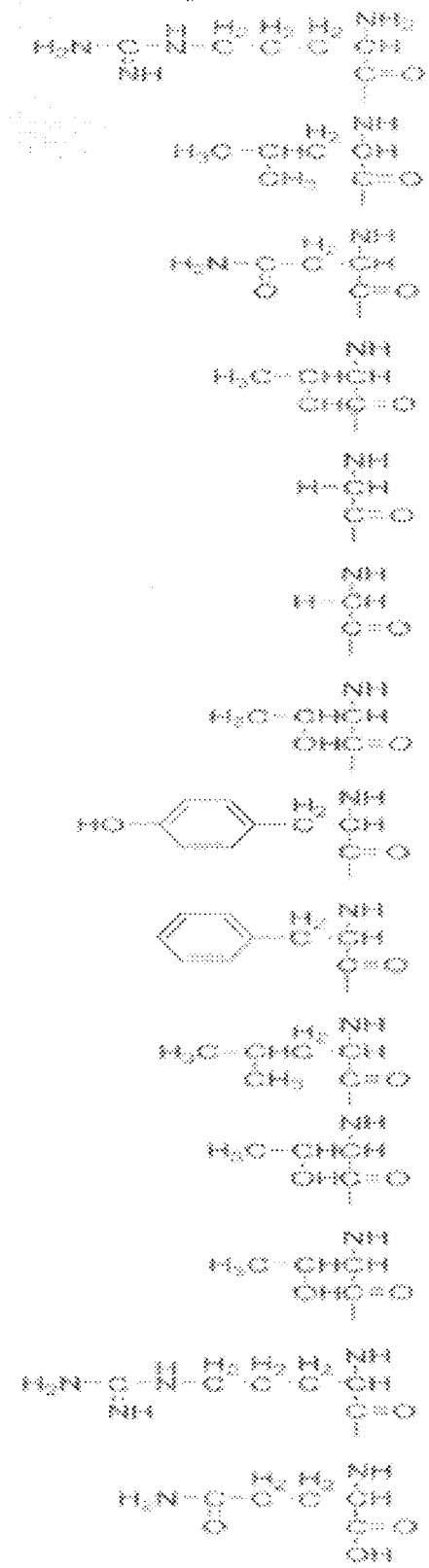
FIG. 1 illustrates a peptide which includes an amino acid sequence represented by SEQ ID NO:1.

The peptide which binds to the glypican-3 protein may contain an amino acid sequence represented by SEQ ID NO:1 or some of the amino acid sequence represented by SEQ ID NO: 1. FIG. 1 illustrates a peptide which includes an amino acid sequence represented by SEQ ID NO:1.

The peptide of the present invention, which contains an amino acid sequence represented by SEQ ID NO:1 or some of the amino acid sequence thereof, recognizes glypican-3 protein as an antigen. Therefore, the peptide may be labeled by image signal materials for diagnosis of tumors, or may bind to anticancer agents to be used for diagnosis and treatment of diseases in which glypican-3 protein is overexpressed.

The glypican-3 protein is a heparin sulfate proteoglycan bound to the cell surface. Glypican-3 protein is known to be very deeply involved in cell division during development or in control of the pattern, and it has been reported that glypican-3 protein is expressed at higher levels in hepatocellular carcinoma than alphafetoprotein (AFP), a hepatocellular carcinoma marker currently in clinical use. In addition, glypican-3 protein is expressed in carcinomas such as melanoma, germ cell tumor, some pulmonary carcinoma and liposarcoma, etc. as well as in hepatocellular carcinoma.

The present invention provides a kit for diagnosis of carcinomas, including the specific peptide binding to glypican-3 protein. Because glypican-3 in a kit for diagnosis of carcinomas of the present invention may be used as a marker for diagnosis of a particular carcinoma, the peptide of the present invention, which specifically binds to glypican-3 may be used to quantify glypican-3.

The peptide, which binds specifically to glypican-3 protein, in the kit for diagnosis may include a label, which may be directly or indirectly detected by spectroscopic, photochemical, biochemical, immunochemical, or chemical means. Preferably, the label may include a material selected from the group consisting of chromogenic enzyme, radioactive isotope, chromophore, luminescent material, and fluorescent material, or mixtures thereof.

The present invention provides a contrast agent for in vivo imaging, including the peptide that binds specifically to glypican-3 protein. Nuclear medical images may be obtained by labeling the peptide that binds specifically to glypican-3 protein with a label, which may be directly or indirectly detected by spectroscopic, photochemical, biochemical, immunochemical, or chemical means. Specifically, nuclear medical images may be obtained by labeling the peptide that binds specifically to glypican-3 of the present invention with a material selected from the group consisting of chromogenic enzyme, radioactive isotope, chromophore, luminescent material, fluorescent material, iron oxide, CT contrast agent, carbon and gold nanoparticles, or mixtures thereof. Specifically, the peptide that binds specifically to GPC-3 protein of the present invention may be labeled by, for example, Tc-99m, In-111, or F-18 which emits gamma-ray, and may be in vivo injected to measure the size and location of tumors by using nuclear medical images obtained. When the peptide of the present invention is labeled by iron oxide which generates magnetic resonance imaging signals, MRI images may be obtained. When the peptide is attached to CT contrast agent or gold nanoparticles, etc., the location and size of tumors may be measured by CT images.

The present invention provides a composition for treatment and prophylaxis of carcinomas, including the peptide that binds specifically to glypican-3 protein. Because the peptide that binds specifically to glypican-3 protein may be used for treatment of carcinomas by being labeled by nuclides for treatment, a composition for treatment and prophylaxis of carcinomas including the peptide may be prepared. Specifically, nuclides for treatment which emits beta-ray, for example, Y-90, I-131, or Re-188 may be used for direct therapeutic effects.

The composition for treatment and prophylaxis of carcinomas may be used in treatment of various malignant tumors including hepatocellular carcinoma, melanoma, germ cell tumor, squamous cell pulmonary carcinoma, colorectal carcinoma, mammary carcinoma, prostatic carcinoma, leukemia, lymphoma, pancreatic carcinoma, or liposarcoma, in which glypican-3 protein is expressed. Preferably, it may be used in treatment for hepatocellular carcinoma, melanoma, or germ cell tumor.

A composition for treatment and prophylaxis of carcinomas of the present invention may be prepared in various formulations including oral and parenteral administration when clinically administered, and used in the form of general pharmaceutical preparation. The preparation may be prepared by using a conventional diluent or excipient such as filler, extender, binder, humectant, disintegrating agent, surfactant, etc., and may be variously formulated in tablet, troche, elixir, suspension, syrup, wafer, and injection, including pharmaceutically acceptable carriers.

The dose of the composition for treatment and prophylaxis of the present invention may differ depending on various factors such as disease type and severity, age, body weight, sensitivity to drugs, type of current therapy, mode of administration, target cell, etc., and may be easily determined by those of ordinary skill in the art.

Figure 2:
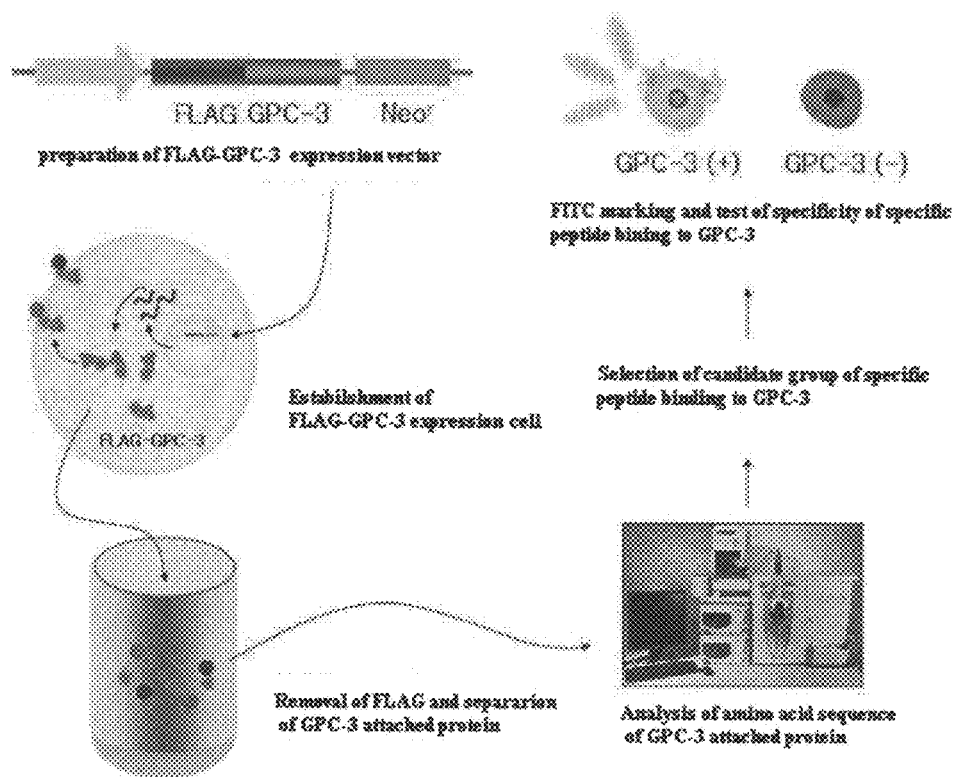
FIG. 2 illustrates a schematic diagram of a process for preparing a peptide that binds specifically to GPC-3 of the present invention, including constructing a FLAG-GPC-3 expression vector, preparing a stable cell line using the same, separating GPC-3 protein, screening a GPC-3 specific ligand, and specifically screening a GPC-3 protein using the corresponding ligand.

FIG. 2 illustrates a preparation method of a peptide that binds specifically to glypican-3 protein of the present invention. According to FIG. 2, the preparation method of the peptide that binds specifically to glypican-3 protein of the present invention includes preparing a FLAG-GPC-3 expression vector (S1); establishing a FLAG-GPC-3 expression vector (S2); separating a GPC-3 attached protein (S3); analyzing amino acid sequences (S4); constructing a peptide (S5); and labeling and testing the specificity of the peptide (S6).

The preparing of the FLAG-GPC-3 expression vector (S1) is a step in which a p3×FLAG-Tagged vector is ligated to construct a FLAG-Tagged GPC-3 vector.

The establishing of the FLAG-GPC-3 expression vector (S2) is a step in which the FLAG-Tagged GPC-3 vector constructed in Step 1 is transfected into a human cell line to construct a FLAG-GPC-3 expression cell. The human cell line may include a human hepatocellular carcinoma cell line or human renal cell line, etc. The FLAG-Tagged GPC-3 vector may be transfected into the human cell line, followed by treatment with antibiotics to construct an antibiotic-resistant FLAG-GPC-3 expression cell.

The separating of the GPC-3 attached protein (S3) is a step in which FLAG antibodies are used in the FLAG-GPC-3 expression cell to obtain only GPC-3-FLAG protein, followed by affinity purification for removal of the FLAG to obtain a pure GPC-3 protein.

The analyzing of the amino acid sequences (S4) is a step in which a ligand bound to the pure GPC-3 protein is separated and the amino acid sequence of the pure GPC-3 protein is analyzed by using LC-ESI-ms/ms tandem mass spectrometry.

The constructing of the peptide (S5) is a step in which a peptide that binds specifically to GPC-3 protein is selected based on the amino acid sequences analyzed in Step 4.

The labeling and testing the specificity of the peptide is a step in which whether the peptide constructed in Step 5 may be specifically bound to GPC-3 is confirmed. The peptide selected in Step 5 may be labeled with a fluorescent material to confirm whether it may bind to GPC-3. The fluorescent material may include FITC.

Hereinafter, the present invention will be described with reference to examples. However, the following examples are provided for illustrative purposes only, and the scope of the present invention should not be limited thereto in any manner.

Example 1

Cell Culture

Human hepatocellular carcinoma cell lines (HepG2, Huh-7), melanoma cell line (SkMe 128), and renal cell line (HEK293, Cos-7) were purchased from American Type Culture Collection, Manassas (ATCC, Manassas, Va., USA) and used. Cells were incubated in D-MEM medium supplemented with 10% fetal bovine serum (Hyclone, Co.) and 1% antibiotic-antimycotic (GIBCO, co.).

Example 2

Amplification of glypican-3 (GPC-3) gene

Human GPC-3 gene was purchased from NGIC (Korea unigene). The gene had been inserted into a pDNR-LIB vector (Clonetech, Mountain View, Calif., USA) and was subjected to gene amplification by polymerase chain reaction (PCR) to obtain a GPC-3 gene with desired restriction enzyme sites XbaI and EcoRI.

The base sequences of a primer for amplification of only a desired site are: forward primer 5'-AATTAGAATTCCAG-GATGGCCGGGACCGTC-3' (SEQ ID NO:8) and reverse primer 5'-TTACTCTAGAGTAGCACATGTGCTGGGCA-3' (SEQ ID NO:9).

Example 3

Construction of a GPC-3 Expression Vector

A GPC-3 product constructed from PCR in Example 2 was ligated to a p3×FLAG-Tagged vector (Sigma-Aldrich, USA) including a cytomegalovirus (CMV) promoter to construct a FLAG-Tagged GPC-3 vector.

Example 4

Introduction of a GPC-3 Expression Vector into a Cell Line

1 μg of the FLAG-Tagged GPC-3 gene in Example 3 was transfected into 1×10$^6$ of human hepatocarcinoma cell line (HepG2) and renal cell line (HEK 293) by using Lipofectamine™ 2000 (Invitrogen Co. Carsbad, Calif., USA), and treated with Geneticin (Invitrogen Co.) at 300, 600, and 800 μg/ml, respectively, for about 2 weeks to allow the proliferation of only resistant cells into which the gene had been introduced. These were referred to as HepG2/GPC-3 and HEK293/GPC-3.

Example 5

Confirmation of HepG2/GPC-3 Cell Line by Reverse Transcriptase-Polymerase Chain Reaction (RT-PCR)

Trizol reagent (invitrogen Co.) was mixed with the cells treated with Geneticin for two weeks in Example 4 for separation of total RNA, followed by M-MuLV reverse enzyme (fermamtas Co. EU) to prepare a cDNA. The cDNA as a template was subjected to polymerase chain reaction (PCR) using a p3×FLAG primer and electrophoresis in a 0.9% agarose gel, followed by staining with ethidium bromide (EtBr) to confirm PCR products. PCR was performed using a GAPDH primer as a positive control group.

Example 6

Confirmation of Protein Expression

Whether glypican-3 is expressed in the hepatocellular carcinoma cell lines HepG2 and Huh-7 cells, the melanoma cell line SkMe128 cell, and renal cell lines HEK293 and Cos-7 cells was confirmed by RTPCR and Western blot. FLAG-Tagged GPC-3 was transfected into the human hepatocellular carcinoma cell line HepG2 cell, and then was constructed as a permanent expression vector to confirm whether GPC-3 protein and FLAG-Tagged GPC-3 protein were expressed by Western blot.

Figure 3:
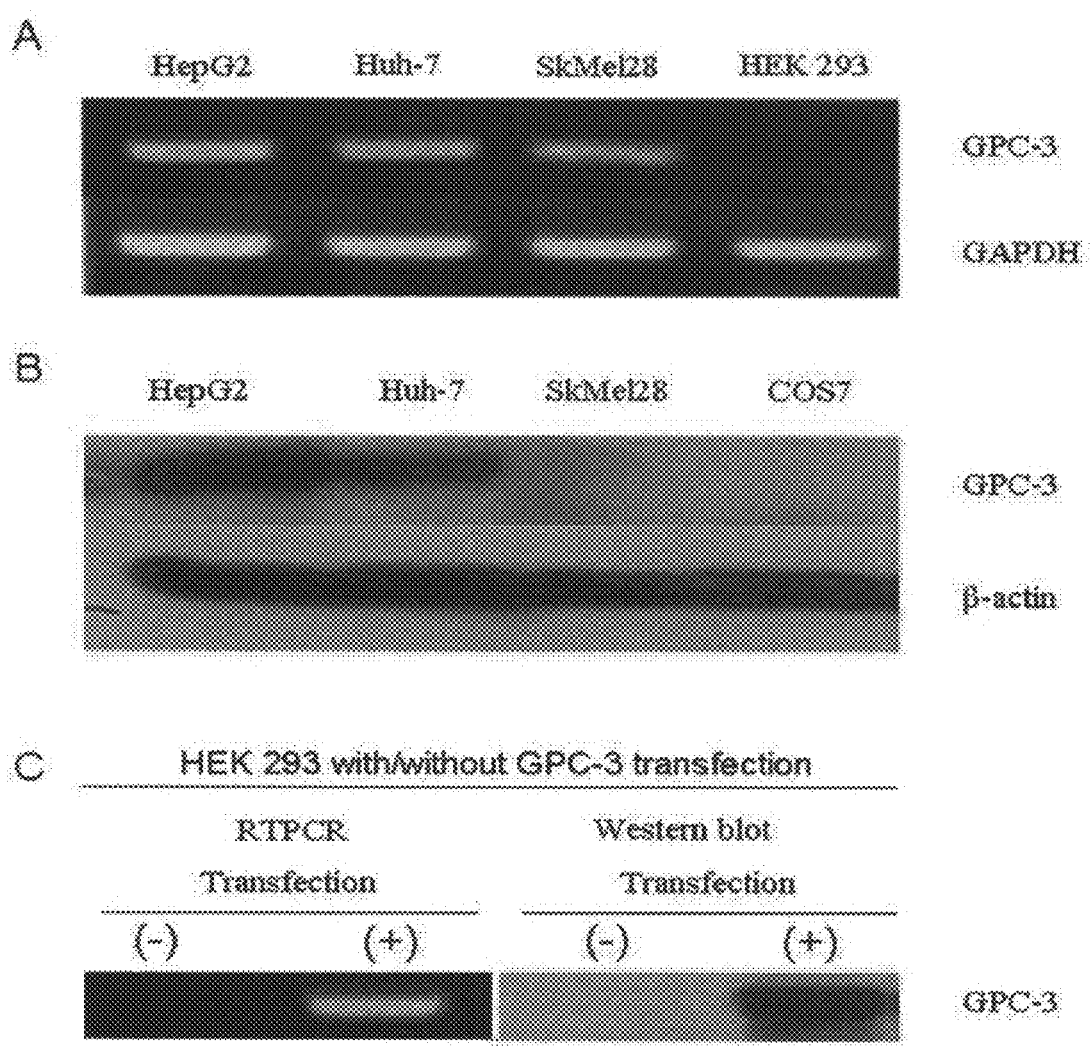
FIG. 3 illustrates results of expression of glypican-3 genes and proteins in the hepatocellular carcinoma cell lines HepG2 and Huh-7 cells, the melanoma cell line SkMe128 cell, the renal cell line HEK293 cell, and Cos-7 cell.
Figure 4:
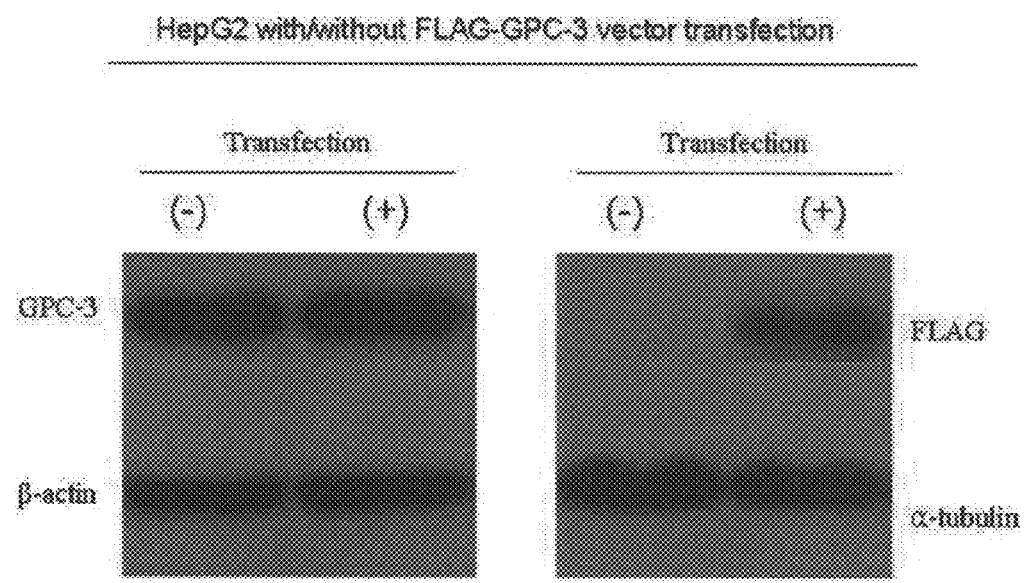
FIG. 4 illustrates results of expression of FLAG-Tagged GPC-3 protein in the human hepatocellular carcinoma cell line HepG2 cell into which FLAG-Tagged GPC-3 gene had been permanently transfected.

The following experiments were performed to observe whether GPC-3 protein was expressed. First, cells were washed with PBS, and then an appropriate amount of a lysis solution (50 mM Tris-Cl pH 8.0, 150 mM NaCl, 5 mM EDTA, 0.5% NP-40, 100 μM PMSF, 1 μg/ml Luepeptin, 1 μg/ml Aprotinin, 1 mM DTT) was used to lysate cells. Reaction was performed on ice for 30 min, followed by centrifugation at 5000 rpm for 30 min to separate proteins from cells. 40 μg of the proteins were subjected to electrophoresis in a 9% acrylamide gel, followed by transfection into a nitrocellulose membrane. Blocking was performed for 1 hour at room temperature with 5% skimmed milk, followed by reaction with a primary antibody (GPC-3 antibody 1: 1000 (biomosaics), p3×FLAG antibody at 10 μg/ml (SIGMA, co.)) overnight at 4° C. The membrane was washed with TBST solution, followed by reaction with a HRP attached secondary antibody for 2 hrs. at room temperature. Again, washing was performed a few times in the TBST solution, and probed by ECL. FIGS. 3 and 4 illustrate the results. Because beta-actin and GAPDH in FIGS. 3 and 4 were house keeping genes and the degree of expression was constant under any conditions, they were used as control groups.

FIG. 3 illustrates test results of expression of glypican-3 genes and proteins in HepG2 and Huh-7 cells, the melanoma cell line SkMe128 cell, the renal cell lines HEK293 and Cos-7 cells. FIG. 3A illustrates a test result of whether GPC-3 gene was expressed using RTPCR, while FIG. 3B illustrates a result from observation of whether GPC-3 gene was expressed by Western blot. According to FIGS. 3A and B, it can be confirmed that GPC-3 protein was expressed in the hepatocellular carcinoma cell lines and the melanoma cell line while GPC-3 protein was not expressed in the renal cell lines. According to FIG. 3C, it can be confirmed that GPC-3 gene and GPC-3 protein were expressed in the human renal cell line HEK 293 cell by transfection of GPC-3 gene.

FIG. 4 illustrates a result of expression of FLAG-Tagged GPC-3 protein in the human hepatocellular carcinoma cell line HepG2 cell into which FLAG-Tagged GPC-3 gene had been permanently transfected. According to FIG. 4, it can be confirmed that FLAG-Tagged GPC-3 gene was expressed only in HepG2 cell line as a human hepatocellular carcinoma cell line into which FLAG-Tagged GPC-3 had been transfected.

Example 7

Separation and Analysis of Ligands which Specifically Bind to GPC-3

Figure 5:
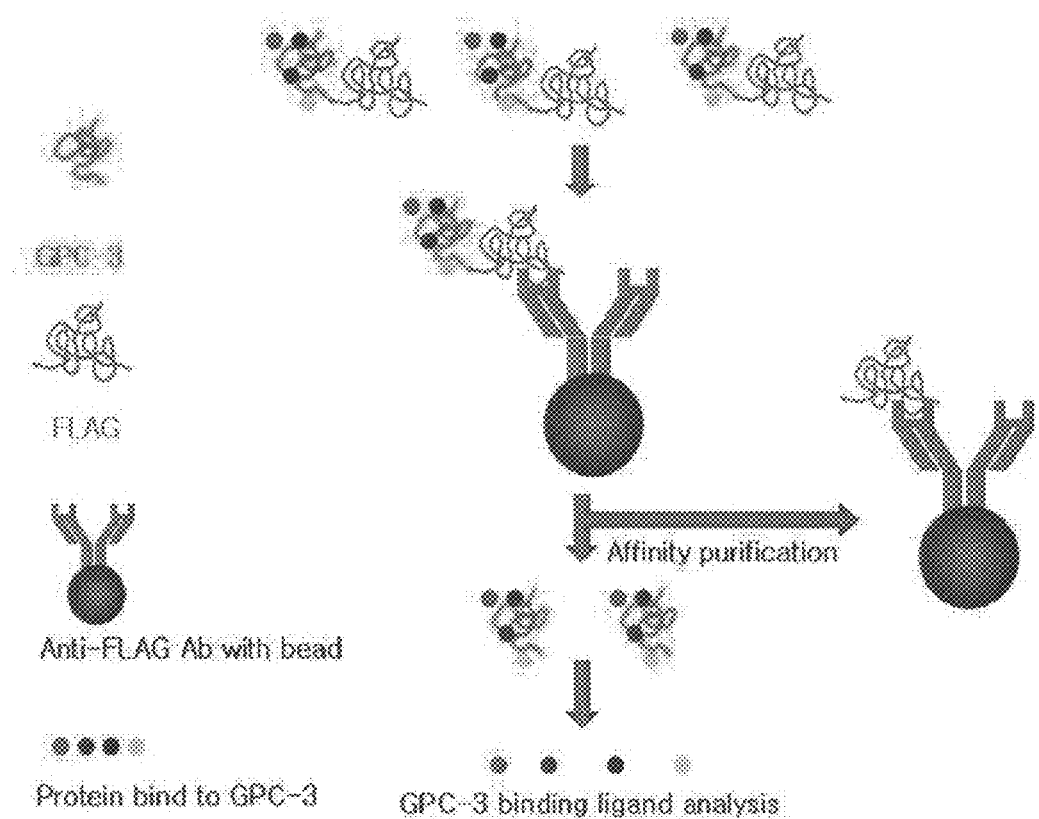
FIG. 5 illustrates a process for separating ligands bound to GPC-3 protein by using FLAG antibody-beads. The left portion of FIG. 5 illustrates the components of the immunopurification process (i.e., FLAG-tagged GPC-3, bead-attached FLAG antibodies (anti-FLAG Ab with bead), and proteins that bind to GPC-3), the right portion of FIG. 5 illustrates a process for separating ligands bound to GPC-3 protein using FLAG-tagged GPC-3 and FLAG antibody-beads. Namely, bead-attached FLAG antibodies were used to pulldown FLAG-tagged GPC-3 and proteins bound to GPC-3. The FLAG tag was removed from GPC-3 and FLAG was removed by affinity purification to obtain a pure GPC-3 protein. The GPC-3 protein was subjected to immunoprecipitation to confirm whether GPC-3 ligands were present.
Figure 6:
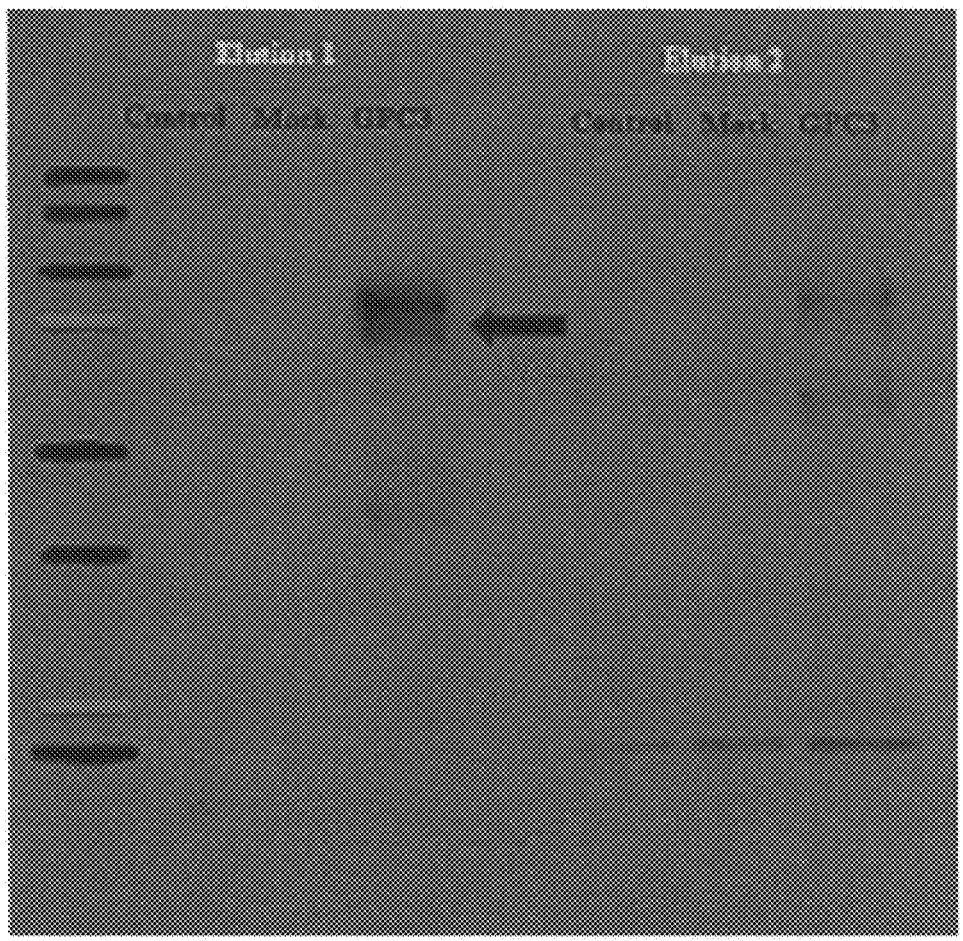
FIG. 6 illustrates electrophoresis results of GPC-3 protein ligands subjected to immunoprecipitation. Elution 1 and Elution 2 represent the first elution of GPC-3 from the FLAG antibody beads and the second elution of GPC-3 from the FLAG antibody beads.

7-1. FIG. 5 illustrates the process of separating ligands which specifically bind to GPC-3 protein. According to FIG. 5, bead-attached FLAG antibodies were used in proteins of HepG2/GPC-3(a GPC-3 expression cell) to separate only GPC-3-FLAG proteins, and then FLAG was removed by affinity purification to obtain a pure GPC-3 protein. The GPC-3 protein was subjected to immunoprecipitation to confirm whether GPC-3 ligands were present. FIG. 6 illustrates a result from confirmation of GPC-3 ligands by electrophoresis.

7-2. Ligands bound to the pure GPC-3 protein were separated, followed by sequencing using LC-ESI-ms/ms tandem mass spectrometry. 56 ligand proteins were obtained.

Example 8

Construction of a Peptide that Binds Specifically to GPC-3

Referring to ligand analysis results using the LC-ESI-ms/ms tandem mass spectrometry method in Example 7, the fluorescent material FITC was attached to a peptide containing the following seven amino acid sequences by using amino acid sequences of plausible candidates BTB/POZ DOMAIN CONTAINING PROTEIN KCTD 5 and EXTRACELLULAR GLYCOPROTEIN LACRITIN PRECURSOR which may specifically bind to GPC-3 for preparation.

```
1. BTB/POZ DOMAIN CONTAINING PROTEIN KCTD 5
B1: FITC-RLNVGGTYFLTTRQ        (SEQ ID No. 1)

B2: FITC-KELHNTPYGTASEPSEKAKI  (SEQ ID No. 2)
```

-continued

```
B3:  FITC-KELHNTPYGTASEPSEKA      (SEQ ID No. 3)

B4:  FITC-RCSAGLGALAQRPGSVDSKW    (SEQ ID No. 4)

B5:  FITC-RGGIGAGLGGGLCRR         (SEQ ID No. 5)

2. EXTRACELLULAR GLYCOPROTEIN LACRITIN
PRECURSOR
L1:  FITC-KQFIENGSEFAQKL          (SEQ ID No. 6)

L2:  FITC-KSILLTEQALAKA           (SEQ ID No. 7)
```

Example 9

Confirmation of Binding Reaction of a Peptide of the Present Invention with GPC-3

Figure 8:
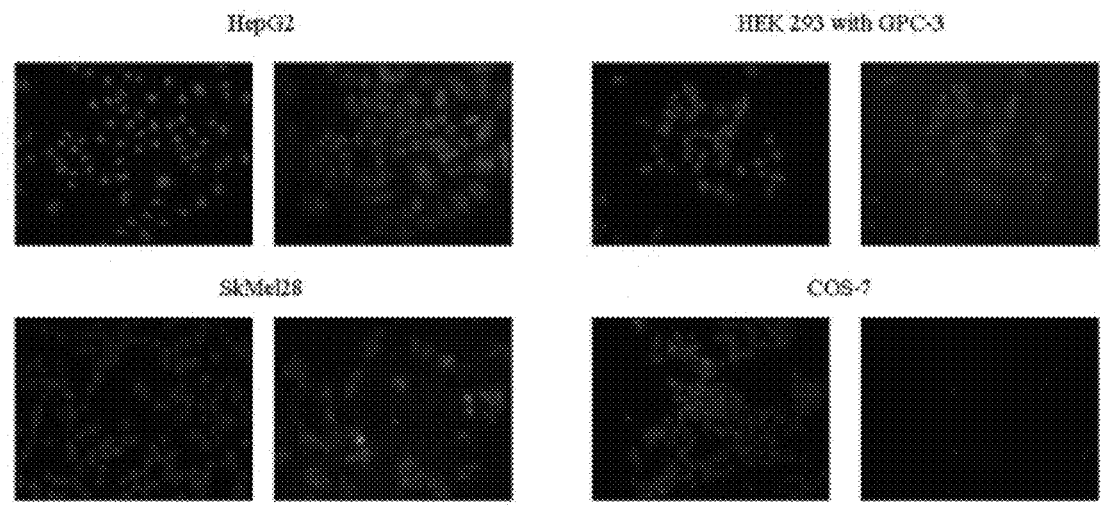
FIG. 8 illustrates overlay results of hepatocellular carcinoma cell line in which GPC-3 protein is expressed (HepG2), melanoma cell line (SkMe128), human renal cell line into which GPC-3 gene was transfected (HEK-293 with GPC-3), and renal cell line in which GPC-3 protein was not expressed (Cos-7) with a peptide represented by some (YFLTTRQ) of a peptide sequence containing an amino acid sequence of SEQ ID NO:1 through labeling of FITC. The images on the left hand side show the cells and the right panel shows the cells labeled by SEQ ID NO:1 FITC if GPC-3 protein is present.
Figure 9:
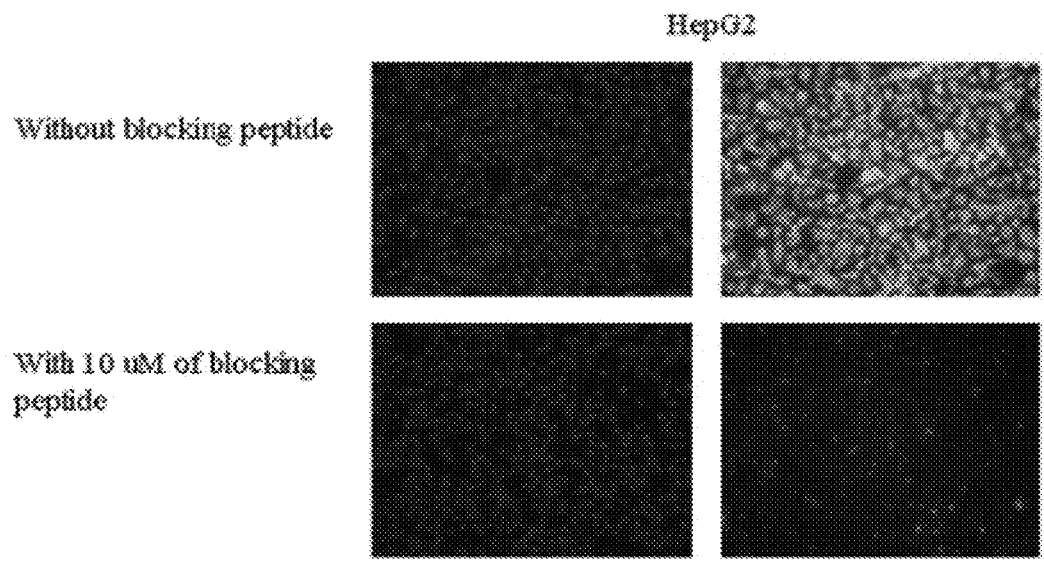
FIG. 9 illustrates comparisons of reaction results of a peptide containing an amino acid sequence of SEQ ID No.1 to the human hepatocellular carcinoma cell line HepG2 through FITC labeling with an equivalent peptide to which FITC was not bound. The images on the left hand side show the cells and the right panel shows the cells labeled by SEQ ID NO:1 FITC if GPC-3 protein is present.

The peptide synthesized in Example 8 was subjected to an overlay assay. First, the human hepatocellular carcinoma cells (HepG2, Huh-7) and the renal cell (HEK293) were cultured to about $1\times10^5$ in an 8-well chamber slide, followed by washing three times with PBS for three min. In order to prevent non-specific reactions, a reaction was performed in Opti-MEM supplemented with 1% BSA for 1 hour. Again, washing was performed three times with PBS for three min, and then cells were fixed with a fixative containing ethanol and acetone at 2:1 for 3 min. The cells were mounted in Mounting medium supplemented with DAPI. FIGS. 8 through 10 illustrate the results.

Figure 7:
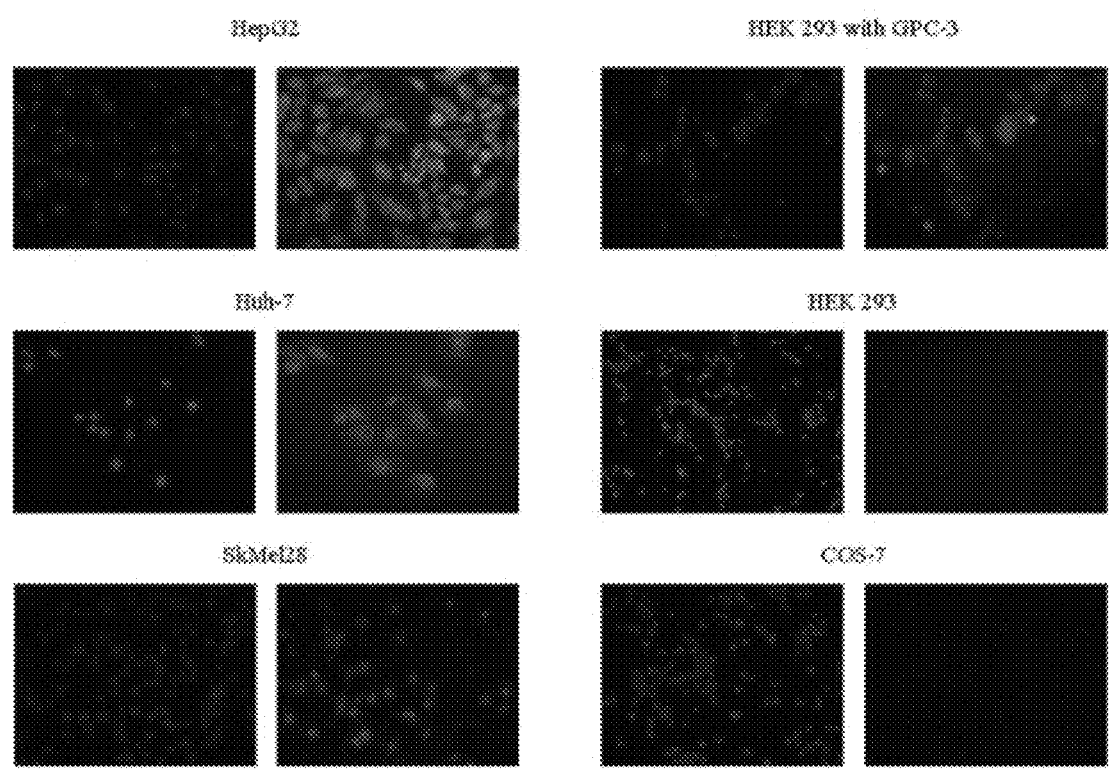
FIG. 7 illustrates overlay results of hepatocellular carcinoma cell lines in which GPC-3 protein was expressed (HepG2, Huh-7), melanoma cell line (SkMe128), human renal cell line into which GPC-3 gene was transfected (HEK-293 with GPC-3), and renal cell lines in which GPC-3 protein was not expressed (HEK-293, Cos-7) with a peptide containing an amino acid sequence of SEQ ID NO:1 through FITC labeling (FITC-RLNVGGTYFLTTRQ). The images on the left hand side show the cells and the right panel shows the cells labeled by SEQ ID NO:1 FITC if GPC-3 protein is present.

FIG. 7 illustrates overlay results of hepatocellular carcinoma cell lines in which GPC-3 protein was expressed (HepG2, Huh-7), melanoma cell line (SkMe128), human renal cell line into which GPC-3 gene was transfected (HEK-293 with GPC-3), and renal cell lines in which GPC-3 protein was not expressed (HEK-293, Cos-7) with a peptide (FITC-RLNVGGTYFLTTRQ) containing the amino acid sequence of SEQ ID NO:1. According to FIG. 7, fluorescence by FITC was observed in all the cell lines in which GPC-3 protein was expressed, while fluorescence was not observed in any of the cells in which GPC-3 protein was not expressed.

FIG. 8 illustrates overlay results of hepatocellular carcinoma cell line in which GPC-3 protein was expressed (HepG2), melanoma cell line (SkMe128), human renal cell line into which GPC-3 gene was transfected (HEK-293 with GPC-3), and renal cell line in which GPC-3 protein was not expressed (Cos-7) with a peptide (FITC-YFLTTRQ) containing some of the amino acid sequence of SEQ ID NO:1. According to FIG. 8, fluorescence by FITC was observed in all the cell lines in which GPC-3 protein was expressed, while fluorescence was not observed in any of the cells in which GPC-3 protein was not expressed.

FIG. 9 illustrates image results obtained from reaction of a peptide (FITC-RLNVGGTYFLTTRQ) containing the amino acid sequence of SEQ ID No.1 to the human hepatocellular carcinoma cell line HepG2 in which GPC-3 protein was expressed with an equivalent peptide to which FITC were not bound. According to FIG. 9, it can be seen that fluorescence was not observed due to inhibition of FITC-labeled peptide bonding. Because a peptide in which a fluorescent material was not labeled and a fluorescent material labeled peptide were competing for bonding to GPC-3 protein, a fluorescent material labeled peptide became less likely to bind to GPC-3. It can be confirmed from these results that the peptide containing the amino acid sequence of SEQ ID NO:1 has specificity to GPC-3.

As observed above, a peptide of the present invention specifically binds to GPC-3 protein overexpressed in carcinoma cells. Therefore, a peptide of the present invention may be used in diagnosis and treatment of carcinomas. A treatment targeting GPC-3 by using a peptide of the present invention would effectively remove only carcinoma cells without harming normal tissues.

A peptide of the present invention may be used in diagnosis and treatment of tumors in which glypican-3 protein is expressed by specifically binding to the glypican-3 protein whose expression increases in carcinoma cells.

A peptide of the present invention may label an image signal material such as radionuclide to be applied for imaging diagnosis and also label a therapeutic material to be applied for treatment.

A peptide of the present invention is so specific that it may be applied for accurate diagnosis and treatment even in the case of small tumors.

Because glypican-3 protein is not highly expressed in normal organs, it may significantly reduce harmful effects on normal organs by agents for treatment of tumors such as anticancer agents when the agents are applied in combination with a peptide of the present invention for treatment.

Exemplary embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. An isolated peptide, that binds specifically to human glypican-3 protein, consisting essentially of SEQ ID NO:1.

2. The isolated peptide of claim 1, that binds specifically to human glypican-3 protein, consisting essentially of a linear sequence of at least seven (7) contiguous amino acids of SEQ ID NO: 1.

3. A kit for identifying a carcinoma, the kit comprising the isolated peptide of claim 1 that binds to human glypican-3 protein, wherein the carcinoma is at least one of hepatocellular carcinoma, melanoma, germ cell tumor, squamous cell pulmonary carcinoma, or liposarcoma.

4. The kit as claimed in claim 3, wherein the isolated peptide that binds specifically to human glypican-3 protein is labeled by a material selected from the group consisting of chromogenic enzyme, radioactive isotope, chromophore, luminescent material, fluorescent material, and mixtures thereof.

5. A contrast agent for in vivo imaging of a carcinoma, comprising the isolated peptide of claim 1 that binds specifically to human glypican-3 protein, wherein the carcinoma is at least one of hepatocellular carcinoma, melanoma, germ cell tumor, squamous cell pulmonary carcinoma, or liposarcoma.

6. The contrast agent as claimed in claim 5, wherein the isolated peptide that binds specifically to human glypican-3 protein is labeled by a material selected from the group consisting of chromogenic enzyme, radioactive isotope, chromophore, luminescent material, fluorescent material, iron oxide, CT contrast agent, carbon, and gold nanoparticles, or mixtures thereof.

7. A kit for diagnosis of a carcinoma, comprising the isolated peptide of claim 2 that binds specifically to human glypican-3 protein, wherein the carcinoma is at least one of hepatocellular carcinoma, melanoma, germ cell tumor, squamous cell pulmonary carcinoma, or liposarcoma.

8. The kit as claimed in claim 7, wherein the isolated peptide that binds specifically to human glypican-3 protein is labeled by a material selected from the group consisting of chromogenic enzyme, radioactive isotope, chromophore, luminescent material, and fluorescent material, or mixtures thereof.

9. A contrast agent for in vivo imaging of a carcinoma, comprising the isolated peptide of claim 2 that binds specifically to human glypican-3 protein wherein the carcinoma is at least one of hepatocellular carcinoma, melanoma, germ cell tumor, squamous cell pulmonary carcinoma, or liposarcoma.

10. The contrast agent as claimed in claim 9, wherein the isolated peptide that binds specifically to human glypican-3 protein is labeled by a material selected from the group consisting of chromogenic enzyme, radioactive isotope, chromophore, luminescent material, fluorescent material, iron oxide, CT contrast agent, carbon, and gold nanoparticles, or mixtures thereof.

* * * * *